US010975033B2

(12) United States Patent
Roberts, II et al.

(10) Patent No.: US 10,975,033 B2
(45) Date of Patent: Apr. 13, 2021

(54) METHODS FOR TREATING INFLAMMATION AND HYPERTENSION WITH γ-KETOALDEHYDE SKAVENGERS

(75) Inventors: L. Jackson Roberts, II, Gallatin, TN (US); Venkataraman Amarnath, Nashville, TN (US); David G. Harrison, Atlanta, GA (US); Annet Kirabo, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 572 days.

(21) Appl. No.: 14/232,615

(22) PCT Filed: Jul. 12, 2012

(86) PCT No.: PCT/US2012/046549
§ 371 (c)(1),
(2), (4) Date: May 6, 2014

(87) PCT Pub. No.: WO2013/010034
PCT Pub. Date: Jan. 17, 2013

(65) Prior Publication Data
US 2014/0256774 A1 Sep. 11, 2014

Related U.S. Application Data

(60) Provisional application No. 61/506,848, filed on Jul. 12, 2011.

(51) Int. Cl.
*A61K 31/137* (2006.01)
*A61K 31/44* (2006.01)
*C07D 213/65* (2006.01)
*C07C 215/50* (2006.01)
*C07C 217/58* (2006.01)

(52) U.S. Cl.
CPC .......... *C07D 213/65* (2013.01); *A61K 31/137* (2013.01); *A61K 31/44* (2013.01); *C07C 215/50* (2013.01); *C07C 217/58* (2013.01)

(58) Field of Classification Search
CPC .... A61K 31/44; A61K 31/137; C07D 213/65; C07C 215/50; C07C 217/58
USPC ................................................. 514/351, 655
See application file for complete search history.

(56) References Cited

U.S. PATENT DOCUMENTS

| 3,740,439 | A | 6/1973 | Hedwall et al. |
| 3,794,734 | A | 2/1974 | Cragoe, Jr. et al. |
| 4,123,537 | A | 10/1978 | Smith et al. |
| 6,043,259 | A | 3/2000 | Dhalla |
| 7,705,054 | B1 | 4/2010 | Roberts et al. |
| 8,178,516 | B2* | 5/2012 | Shapiro ............ A61K 31/195 514/162 |
| 8,410,068 | B2* | 4/2013 | Zargari ............ A61P 3/02 514/44 R |

FOREIGN PATENT DOCUMENTS

| EP | 0839799 A1 | 4/1999 |
| WO | WO19960036591 A1 | 11/1996 |
| WO | 2002036109 A3 | 5/2002 |
| WO | 2003045338 | 6/2003 |

OTHER PUBLICATIONS

Kirabo et al. Effect of hypertension on dendritic cells and a potential roel of isoketals. FASEB Journal, Apr. 2010, vol. 24. Meeting Inf: Conference on Experimental Biology. Anaheim, CA, USA. Apr. 24-28, 2010. abstract.*
Agostinho, P., Cunha, R.A., and Oliveira, C. Neuroinflammation, oxidative stress and the pathogenesis of Alzheimer's disease. Curr Pharm Des 16, 2766-2778.
Moore, K.P., Holt, S.G., Patel, R.P., Svistunenko, D.A., Zackert, W., Goodier, D., Reeder, B.J., Clozel, M., Anand, R., Cooper, C.E., et al. (1998). A causative role for redox cycling of myoglobin and its inhibition by alkalinization in the pathogenesis and treatment of rhabdomyolysis-induced renal failure. J Biol Chem 273, 31731-31737.
Holt, S., Reeder, B., Wilson, M., Harvey, S., Morrow, J.D., Roberts, L.J., 2nd, and Moore, K. (1999). Increased lipid peroxidation in patients with rhabdomyolysis. Lancet 353, 1241.
Mukherjee, A., Hale, V.G., Borga, O., and Stein, R. (1996). Predictability of the clinical potency of NSAIDs from the preclinical pharmacodynamics in rats. Inflamm Res 45, 531-540.
Stathopoulos, G.T., Sherrill, T.P., Han, W., Sadikot, R.T., Polosukhin, V.V., Fingleton, B., Yull, F.E., and Blackwell, T.S. (2008). Use of bioluminescent imaging to investigate the role of nuclear factor-kappaBeta in experimental non-small cell lung cancer metastasis. Clin Exp Metastasis 25, 43-51.
Sadikot, R.T., and Blackwell, T.S. (2008). Bioluminescence: imaging modality for in vitro and in vivo gene expression. Methods Mol Biol 477, 383-394.
Wong, E.T., and Tergaonkar, V. (2009). Roles of NF-kappaB in health and disease: mechanisms and therapeutic potential. Clin Sci (Lond) 116, 451-465.
Davies, S.S., Amarnath, V., Brame, C.J., Boutaud, O., and Roberts, L.J., 2nd. (2007). Measurement of chronic oxidative and inflammatory stress by quantification of isoketal/levuglandin gamma-ketoaldehyde protein adducts using liquid chromatography tandem mass spectrometry. Nat Protoc 2, 2079-2091.
Kasuga, K., Yang, R., Porter, T.F., Agrawal, N., Petasis, N.A., Irimia, D., Toner, M., and Serhan, C.N. (2008). Rapid appearance of resolvin precursors in inflammatory exudates: novel mechanisms in resolution. J Immunol 181, 8677-8687.

(Continued)

*Primary Examiner* — Jared Barsky

(74) *Attorney, Agent, or Firm* — Stites & Harbison PLLC; Richard S. Myers, Jr.

(57) ABSTRACT

A method of treating at least one of inflammation, psoriasis, and/or hypertension comprising administering to a patient in need there of an effective gamma-ketoaldehyde scavenging amount of a gamma-ketoaldehyde scavenging compound.

5 Claims, 5 Drawing Sheets

(56) References Cited

OTHER PUBLICATIONS

Davies, Sean S., et al., Pyridoxamine and analogues scavenge lipid-derived gamma-ketoaldehydes and protect against H2O2-mediated cytotoxicity; Biochemistry; Dec. 26, 2006; 45(51); pp. 15756-15767.

Ajuebor, M.N., Singh, A., and Wallace, J.L. (2000). Cyclooxygenase-2-derived prostaglandin D(2) is an early anti-inflammatory signal in experimental colitis. Am J Physiol Gastrointest Liver Physiol 279, G238-244.

Bonazzi, A., Bolla, M., Buccellati, C., Hernandez, A., Zarini, S., Vigano, T., Fumagalli, F., Viappiani, S., Ravasi, S., Zannini, P., et al. (2000). Effect of endogenous and exogenous prostaglandin E(2) on interleukin-1 beta-induced cyclooxygenase-2 expression in human airway smooth-muscle cells. Am J Respir Crit Care Med 162, 2272-2277.

Caggiano, A.O., and Kraig, R.P. (1999). Prostaglandin E receptor subtypes in cultured rat microglia and their role in reducing lipopolysaccharide-induced interleukin-1beta production. J Neurochem 72, 565-575.

Gilroy, D.W., Colville-Nash, P.R., Willis, D., Chivers, J., Paul-Clark, M.J., and Willoughby, D.A. (1999). Inducible cyclooxygenase may have anti-inflammatory properties. Nat Med 5, 698-701.

Giri, S., Rattan, R., Singh, A.K., and Singh, I. (2004). The 15-deoxy-delta12,14-prostaglandin J2 inhibits the inflammatory response in primary rat astrocytes via down-regulating multiple steps in phosphatidylinositol 3-kinase-Akt-NF-kappaB-p300 pathway independent of peroxisome proliferator-activated receptor gamma. J Immunol 173, 5196-5208.

Hashimoto, K., Ethridge, R.T., Saito, H., Rajaraman, S., and Evers, B.M. (2003). The PPARgamma ligand, 15d-PGJ2, attenuates the severity of cerulein-induced acute pancreatitis. Pancreas 27, 58-66.

Haworth, O., and Buckley, C.D. (2007). Resolving the problem of persistence in the switch from acute to chronic inflammation. Proc Natl Acad Sci U S A 104, 20647-20648.

Hilliard, M., Frohnert, C., Spillner, C., Marcone, S., Nath, A., Lampe, T., Fitzgerald, D.J., and Kehlenbach, R.H. The anti-inflammatory prostaglandin 15-deoxy-delta(12,14)-PGJ2 inhibits CRM1-dependent nuclear protein export. J Biol Chem 285, 22202-22210.

Ianaro, A., Ialenti, A., Maffia, P., Di Meglio, P., Di Rosa, M., and Santoro, M.G. (2003). Anti-inflammatory activity of 15-deoxy-delta12,14-PGJ2 and 2-cyclopenten-1-one: role of the heat shock response. Mol Pharmacol 64, 85-93.

Idzko, M., Hammad, H., van Nimwegen, M., Kool, M., Vos, N., Hoogsteden, H.C., and Lambrecht, B.N. (2007). Inhaled iloprost suppresses the cardinal features of asthma via inhibition of airway dendritic cell function. J Clin Invest 117, 464-472.

Jiang, G.L., Im, W.B., Donde, Y., and Wheeler, L.A. Comparison of prostaglandin E2 receptor subtype 4 agonist and sulfasalazine in mouse colitis prevention and treatment. J Pharmacol Exp Ther 335, 546-552.

Min, S.Y., Kim, W.U., Cho, M.L., Hwang, S.Y., Park, S.H., Cho, C.S., Kim, J.M., and Kim, H.Y. (2002). Prostaglandin E2 suppresses nuclear factor-kappaB mediated interleukin 15 production in rheumatoid synoviocytes. J Rheumatol 29, 1366-1376.

Mochizuki, M., Ishii, Y., Itoh, K., Iizuka, T., Morishima, Y., Kimura, T., Kiwamoto, T., Matsuno, Y., Hegab, A.E., Nomura, A., et al. (2005). Role of 15-deoxy delta(12,14) prostaglandin J2 and Nrf2 pathways in protection against acute lung injury. Am J Respir Crit Care Med 171, 1260-1266.

Muller, T., Durk, T., Blumenthal, B., Herouy, Y., Sorichter, S., Grimm, M., Panther, E., Cicko, S., Norgauer, J., and Idzko, M. Iloprost has potent anti-inflammatory properties on human monocyte-derived dendritic cells. Clin Exp Allergy 40, 1214-1221.

Park, E.J., Park, S.Y., Joe, E.H., and Jou, I. (2003). 15d-PGJ2 and rosiglitazone suppress Janus kinase-STAT inflammatory signaling through induction of suppressor of cytokine signaling 1 (SOCS1) and SOCS3 in glia. J Biol Chem 278, 14747-14752.

Pirianov, G., Waddington, S.N., Lindstrom, T.M., Terzidou, V., Mehmet, H., and Bennett, P.R. (2009). The cyclopentenone 15-deoxy-delta 12,14-prostaglandin J(2) delays lipopolysaccharide-induced preterm delivery and reduces mortality in the newborn mouse. Endocrinology 150, 699-706.

Rajakariar, R., Hilliard, M., Lawrence, T., Trivedi, S., Colville-Nash, P., Bellingan, G., Fitzgerald, D., Yaqoob, M.M., and Gilroy, D.W. (2007). Hematopoietic prostaglandin D2 synthase controls the onset and resolution of acute inflammation through PGD2 and 15-deoxyDelta12 14 PGJ2. Proc Natl Acad Sci U S A 104, 20979-20984.

Scher, J.U., and Pillinger, M.H. (2009). The anti-inflammatory effects of prostaglandins. J Investig Med 57, 703-708.

Soberman, R.J., and Christmas, P. (2006). Revisiting prostacyclin: new directions in pulmonary fibrosis and inflammation. Am J Physiol Lung Cell Mol Physiol 291, L142-143.

Strassheim, D., Riddle, S.R., Burke, D.L., Geraci, M.W., and Stenmark, K.R. (2009). Prostacyclin inhibits IFN-gamma-stimulated cytokine expression by reduced recruitment of CBP/p300 to STAT1 in a SOCS-1-independent manner. J Immunol 183, 6981-6988.

Takagi, T., Naito, Y., Ichikawa, H., Tomatsuri, N., Katada, K., Isozaki, Y., Kuroda, M., Kokura, S., Yoshida, N., and Yoshikawa, T. (2004). A PPAR-gamma ligand, 15-deoxy-Delta12,14-prostaglandin J(2), inhibited gastric mucosal injury induced by ischemia-reperfusion in rats. Redox Rep 9, 376-381.

Takahashi, Y., Tokuoka, S., Masuda, T., Hirano, Y., Nagao, M., Tanaka, H., Inagaki, N., Narumiya, S., and Nagai, H. (2002). Augmentation of allergic inflammation in prostanoid IP receptor deficient mice. Br J Pharmacol 137, 315-322.

Takaishi, O., Arakawa, T., Fujiwara, Y., Fukuda, T., Otani, K., Yamasaki, K., Higuchi, K., and Kuroki, T. (1999). Inhibition by 16,16-dimethyl prostaglandin E2 of tumor necrosis factor-alpha and interleukin-1beta production and messenger RNA expression in human monocytes stimulated by Helicobacter pylori. Dig Dis Sci 44, 2405-2411.

Ulivi, V., Cancedda, R., and Cancedda, F.D. (2008). 15-deoxy-delta 12,14-prostaglandin J(2) inhibits the synthesis of the acute phase protein SIP24 in cartilage: Involvement of COX-2 in resolution of inflammation. J Cell Physiol 217, 433-441.

Vong, L., Ferraz, J.G., Panaccione, R., Beck, P.L., and Wallace, J.L. A pro-resolution mediator, prostaglandin D(2), is specifically up-regulated in individuals in long-term remission from ulcerative colitis. Proc Natl Acad Sci U S A 107, 12023-12027.

Vunta, H., Davis, F., Palempalli, U.D., Bhat, D., Arner, R.J., Thompson, J.T., Peterson, D.G., Reddy, C.C., and Prabhu, K.S. (2007). The anti-inflammatory effects of selenium are mediated through 15-deoxy-Delta12,14-prostaglandin J2 in macrophages. J Biol Chem 282, 17964-17973.

Zhou, W., Hashimoto, K., Goleniewska, K., O'Neal, J.F., Ji, S., Blackwell, T.S., Fitzgerald, G.A., Egan, K.M., Geraci, M.W., and Peebles, R.S., Jr. (2007). Prostaglandin I2 analogs inhibit proinflammatory cytokine production and T cell stimulatory function of dendritic cells. J Immunol 178, 702-710.

Zimmer, M., Lamb, J., Ebert, B.L., Lynch, M., Neil, C., Schmidt, E., Golub, T.R., and Iliopoulos, O. The connectivity map links iron regulatory protein-1-mediated inhibition of hypoxia-inducible factor-2a translation to the anti-inflammatory 15-deoxy-delta12,14-prostaglandin J2. Cancer Res 70, 3071-3079.

Flower, R.J., Harvey, E.A., and Kingston, W.P. (1976). Inflammatory effects of prostaglandin D2 in rat and human skin. Br J Pharmacol 56, 229-233.

Kingston, W.P., and Greaves, M.W. (1985). Actions of prostaglandin E2 metabolites on skin microcirculation. Agents Actions 16, 13-14.

Salomon, R.G., and Miller, D.B. (1985). Levuglandins: isolation, characterization, and total synthesis of new secoprostanoid products from prostaglandin endoperoxides. Adv Prostaglandin Thromboxane Leukot Res 15, 323-326.

Brame, C.J., Salomon, R.G., Morrow, J.D., and Roberts, L.J., 2nd. (1999). Identification of extremely reactive gamma-ketoaldehydes (isolevuglandins) as products of the isoprostane pathway and characterization of their lysyl protein adducts. J Biol Chem 274, 13139-13146.

(56) References Cited

OTHER PUBLICATIONS

Dinarello, C.A. Anti-inflammatory Agents: Present and Future. Cell 140, 935-950.
Gill, R., Tsung, A., and Billiar, T. Linking oxidative stress to inflammation: Toll-like receptors. Free Radic Biol Med 48, 1121-1132.
Iyer, R.S., Ghosh, S., and Salomon, R.G. (1989). Levuglandin E2 crosslinks proteins. Prostaglandins 37, 471-480.
Murthi, K.K., Friedman, L.R., Oleinick, N.L., and Salomon, R.G. (1993). Formation of DNA-protein cross-links in mammalian cells by levuglandin E2. Biochemistry 32, 4090-4097.
Morrow, J.D., Hill, K.E., Burk, R.F., Nammour, T.M., Badr, K.F., and Roberts, L.J., 2nd. (1990). A series of prostaglandin F2-like compounds are produced in vivo in humans by a non-cyclooxygenase, free radical-catalyzed mechanism. Proc Natl Acad Sci U S A 87, 9383-9387.
Bernoud-Hubac, N., Fay, L.B., Armarnath, V., Guichardant, M., Bacot, S., Davies, S.S., Roberts, L.J., 2nd, and Lagarde, M. (2004). Covalent binding of isoketals to ethanolamine phospholipids. Free Radic Biol Med 37, 1604-1611.
Sullivan, C.B., Matafonova, E., Roberts, L.J., 2nd, Amarnath, V., and Davies, S.S. Isoketals form cytotoxic phosphatidylethanolamine adducts in cells. J Lipid Res 51, 999-1009.
Li, W., Laird, J.M., Lu, L., Roychowdhury, S., Nagy, L.E., Zhou, R., Crabb, J.W., and Salomon, R.G. (2009). Isolevuglandins covalently modify phosphatidylethanolamines in vivo: detection and quantitative analysis of hydroxylactam adducts. Free Radic Biol Med 47, 1539-1552.
Davies, S.S., Amarnath, V., Montine, K.S., Bernoud-Hubac, N., Boutaud, O., Montine, T.J., and Roberts, L.J., 2nd. (2002). Effects of reactive gamma-ketoaldehydes formed by the isoprostane pathway (isoketals) and cyclooxygenase pathway (levuglandins) on proteasome function. FASEB J 16, 715-717.
Cullen, S.J., Ponnappan, S., and Ponnappan, U. Proteasome inhibition up-regulates inflammatory gene transcription induced by an atypical pathway of NF-kappaB activation. Biochem Pharmacol 79, 706-714.
Chou, M.Y., Hartvigsen, K., Hansen, L.F., Fogelstrand, L., Shaw, P.X., Boullier, A., Binder, C.J., and Witztum, J.L. (2008). Oxidation-specific epitopes are important targets of innate immunity. J Intern Med 263, 479-488.
Binder, C.J. Natural IgM antibodies against oxidation-specific epitopes. J Clin Immunol 30 Suppl 1, S56-60.
Talati, M., Meyrick, B., Peebles, R.S., Jr., Davies, S.S., Dworski, R., Mernaugh, R., Mitchell, D., Boothby, M., Roberts, L.J., 2nd, and Sheller, J.R. (2006). Oxidant stress modulates murine allergic airway responses. Free Radic Biol Med 40, 1210-1219.
Kang, Y.J., and Zhou, Z. (2005). Zinc prevention and treatment of alcoholic liver disease. Mol Aspects Med 26, 391-404.
Mottaran, E., Stewart, S.F., Rolla, R., Vay, D., Cipriani, V., Moretti, M., Vidali, M., Sartori, M., Rigamonti, C., Day, C.P., et al. (2002). Lipid peroxidation contributes to immune reactions associated with alcoholic liver disease. Free Radic Biol Med 32, 38-45.
Amarnath, V., Amarnath, K., Davies, S., and Roberts, L.J., 2nd. (2004). Pyridoxamine: an extremely potent scavenger of 1,4-dicarbonyls. Chem Res Toxicol 17, 410-415.
Zagol-Ikapitte, I., Amarnath, V., Bala, M., Roberts, L.J., 2nd, Oates, J.A., and Boutaud, O. Characterization of scavengers of gamma-ketoaldehydes that do not inhibit prostaglandin biosynthesis. Chem Res Toxicol 23, 240-250.
Nahrendorf, M., Pittet, M.J., and Swirski, F.K. Monocytes: protagonists of infarct inflammation and repair after myocardial infarction. Circulation 121, 2437-2445.
Kurien, et al., Autoimmunity and oxidatively modified autoantigens; Autoimmunity Reviews; 7; 2008; pp. 567-573.
Kurien, et al., Oxidatively modified autoantigens in autoimmune diseases; Free Radical Biology & Medicine; 41; 2006; pp. 549-556.
Salomon, et al., Isolevuglandin-protein adducts in humans: products of free radical-induced lipid oxidation through the isoprostane pathway; Biochimica, et al., 485; 2000; pp. 225-235.
Ryan, The pathophysiology of hypertension in systemic lupus erythematosus; Am J Physiol Regal Integr comp Physiol; 2009; 296; pp. R1258-R1267.
Christophers; Psoriasis—epidemiology and clinical spectrum; Clinical and Experimental Dermatology; 2001; 26; pp. 314-320.
Vaziri, et al., Oxidative Stress in Uremia: Nature, Mechanisms, and Potential Consequences; Seminars in Nephrology; 2014; 24; pp. 469-473.
Nakajima, et al., Selective y-ketoaldehyde scavengers protect Nav1.5 from oxidant-induced inactivation; Journal of Moleculare and Cellular Cardiology; 48; 2010; pp. 352-359.
Zagol-Ikapitte, et al., Determination of the Pharmacokinetics and Oral Bioavailability of Salicylamine, a Potent y-Ketoaldehyde Scavenger, by LC/MS/MS; Pharmaceutics; 2010; 2; pp. 18-29.
Sugano, et al., Cyclosporin A inhibits H2Ox-induced apoptosis of human fibroblasts; FEBS Letters; 447; 1999; pp. 274-276.
Manna, et al., Immunosuppressive Leflunomide Metabolite (A77 1726) Blocks TNF-Dependent Nuclear Factor-kB Activation and Gene Expression; Journal of Immunology; 162; 1999; pp. 2095-2102.

\* cited by examiner 2 hr edema: p = 0.0001 for salicylamine
3 hr edema: p = 0.000008 for salicylamine
4 hr edema: p = 0.00005 for salicyalmine

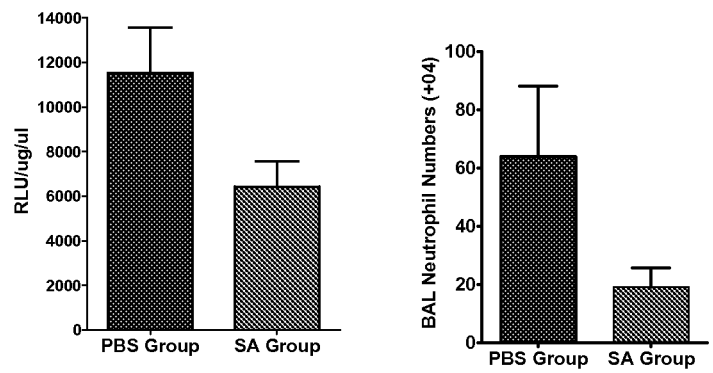
Figure 10
Figure 11
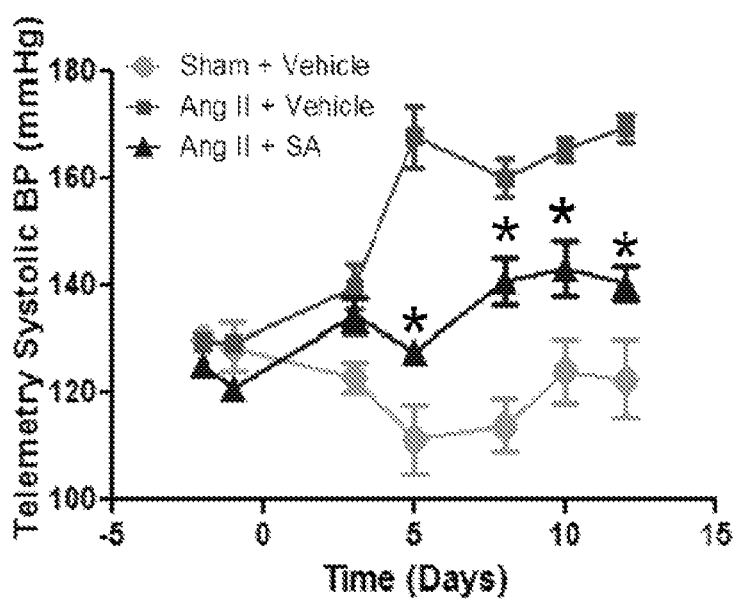
Figure 12

//
US 10,975,033 B2

METHODS FOR TREATING INFLAMMATION AND HYPERTENSION WITH γ-KETOALDEHYDE SKAVENGERS

RELATED APPLICATIONS

This application is a submission under 35 U.S.C. § 371 of International Application No. PCT/US2012/46549, filed Jul. 12, 2012, which claims benefit of US Application No. 61/506,848, filed Jul. 12, 2011, the contents of which are incorporated herein by reference.

GOVERNMENT SUPPORT

This invention was made with government support under grant number GM042056 awarded by the National Institutes of Health. The government has certain rights in the invention.

FIELD OF THE INVENTION

The present invention relates generally to the field of treating and preventing inflammation, and more specifically to the field of controlling isoketals and neuroketals.

The present invention also relates to the field of treating and preventing hypertension, and more specifically treating and preventing hypertension by controlling isoketals and neuroketals.

The present invention also relates to the field of treating and preventing psoriasis, and more specifically treating and preventing psoriasis by controlling isoketals and neuroketals.

BACKGROUND OF THE INVENTION

A major problem that underpins a variety of diseases is inflammation. While many pharmacological approaches have been used to suppress inflammation and many new approaches are being developed, such as inhibitors of inflammatory cytokines, etc., a mainstay in the treatment inflammation for decades has focused on preventing the formation of prostaglandins by inhibiting cyclooxygenase (COX) enzymes with non-steroidal antiiflammatory drugs (NSAID's). While this approach has been effective there are serious drawbacks to the use of both non-selective and selective COX-2 inhibitors. A major complication with chronic use of non-selective COX inhibitors is their propensity to cause gastric ulcers. The development of selective COX-2 inhibitors was initially touted to be major advance in that these agents did not inhibit COX-1 in the stomach, therefore greatly lowering the risk of the development of gastric ulcers. However, selective COX-2 inhibitors do not inhibit platelet thromboxane production but do inhibit prostacyclin production, which results in a pro-thrombotic propensity. In this regard, clinical trials with Rofecoxib were associated with a higher incidence of myocardial infarction, which resulted in its withdrawal from the market.

The underpinning rationale for development of inhibitors of COX enzymes is that the end product prostaglandins (PGs) formed by PG synthases are proinflammatory and therefore inhibiting PG formation by inhibiting COXs would be antiiflammatory. However, there is a major problem with this theory which is that the equivalent of Koch's postulates have never been fulfilled to support this assumption. What is meant by this is that while NSAID's exert antiinflammatory effects, nobody has shown that the PGs produced by the various PG synthases, either singly or in combination, actually induce all aspects of inflammation. In fact, potent antiinflammatory effects have been ascribed to many of the PG's that are formed including $PGD_2$, $PGE_2$, $PGJ_2$, and $PGI_2$[1-28]. The historical basis for the assumption that PGs are inflammatory derives from experiments performed decades ago showing that injection of $PGE_2$ or $PGD_2$ into the skin increased vascular permeability induced by injection of bradykinin or histamine[29; 39]. However, there was no documentation that this was associated with an inflammatory cellular infiltrate so this observation could simply be explained solely by enhanced fluid transudation from capillaries when the two potent vasodilators were co-injected.

What has largely been ignored was the demonstration by Salomon and colleagues several years ago that the endoperoxide intermediate in the cyclooxygenase pathway, $PGH_2$, non-enzymatically rearranges to form highly reactive acyclic γ-ketoaldehydes (γ-KAs), which were termed levuglandins (LGs)[31]. Moreover, the present inventors have also shown that LG-like compounds (termed IsoLGs or isoketals (IsoKs) are also formed in abundance via the isoprostane pathway of non-enzymatic free radical catalyzed oxidation of arachidonic acid[32]. In the setting of inflammation, which is associated enhanced formation of products of COX's and formation of products of the IsoP pathway due to enhanced free radical generation by leukocytes and other sources, the present inventors discovered that the antiinflammatory effects of NSAID's can be largely attributed to inhibition of the formation of LGs and that IsoKs also contribute to inflammation. Accordingly, without being bound by theory or mechanism, the present inventors discovered selective scavengers of these γ-KAs that exert antiinflammatory effects without inhibiting the formation of antiinflammatory PG's. Thus, the compounds of the present invention do not present the adverse effects attributed to chronic NSAID use.

Summary of several abbreviations used herein: $F_2$-isoprostane ($F_2$-IsoP), $F_4$-neuroprostane ($F_4$-NeuroP), isoketal (IsoK), neuroketal (NeuroK), 4-hydroxynonenal (HNE), Alzheimer's disease (AD), arachidonic acid (AA), docosahexaenoic acid (DHA), amyloid precursor protein (APP), amyloid beta (Aβ), paired helical filament (PHF), neurofibrillary tangles (NFT), pyridoxamine (PM), salicylamine (SA), apolipoprotein E (ApoE), vascular dementia (VaD), dementia with Lewy bodies (DLB), multisystem atrophy (MSA), transgenic (Tg), homocysteine (HCys), liquid chromatography (LC), electrospray ionization (ESI), mass spectrometry (MS), collisional induced dissociation (CID), cerebrospinal fluid (CSF).

Isoketals are the most reactive products of lipid peroxidation heretofore identified. IsoKs adduct almost instantaneously to protein lysine residues and readily induce protein-protein cross-links. In spite of the remarkable reactivity of IsoKs, the present inventors have identified compounds that effectively intercept (scavenge) IsoKs from adducting to proteins.

The IsoK scavengers of the present invention are compounds of the present invention, such as salicylamine (SA), for example, and analogs thereof. The compounds of the present invention prevent cell death in cells exposed to a lethal concentration of a general oxidant-hydrogen peroxide.

As indicated herein, IsoKs are a major mediator of oxidant induced cell injury/death. Additionally, as indicated herein, therapeutic use of the IsoK scavengers of the present invention have beneficial effects in a wide variety of diseases associated with oxidative injury.

DESCRIPTION OF THE FIGURES

FIG. 10 is graph that shows reduction of NF-κB activity.
FIG. 11 is graph that shows reduction of neutrophil cell counts.
FIG. 12 is graph that shows reduction in hypertension.

DESCRIPTION OF THE INVENTION

Figure 1:
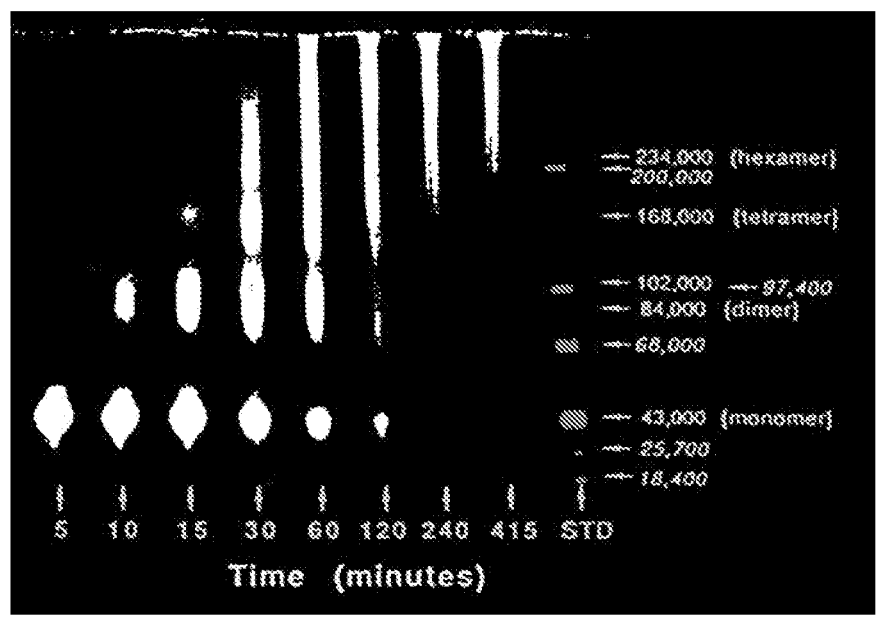
FIG. 1 shows γ-KA induced cross-linking of proteins, analyzed by gel electrophoresis.

One embodiment of the present invention is a novel method of treating inflammation.

Another embodiment of the present invention is methods of treating inflammation by the administration of at least one compound of the present invention.

Embodiments of the present invention are innovative in that they challenge the dogma that has been accepted for decades, which is that NSAID's are antiinflammatory because they inhibit the formation of end product PGs formed via the various PG synthases.

Embodiments of the present invention show that γ-KA scavengers are at least as effective as standard NSAID's, which could lead to the development of new antiinflammatory drugs that are largely devoid of the adverse effects of the standard NSAID's that are widely used today.

Inflammation underpins the pathogenesis of a plethora of human diseases ranging from wounds and infections, inflammatory bowel diseases, psoriasis, diabetes, atherosclerosis, asthma, various forms of arthritis, and neurodegenerative diseases. Nonetheless, current and prior art approaches to diminish the levels of inflammation are currently very limited. These include treatment with NSAIDs and corticosteroids, both of which have substantial and serious side effects. Non-selective NSAID's have a strong propensity to (a) cause gastric ulceration, (b) reduce renal function in patients with impaired renal function, and (c) cause bleeding due to inhibition of platelet function. Selective inhibitors of COX-2 don't have the propensity to cause gastric ulceration but they are associated with a higher incidence of myocardial infarction, which led to withdrawal of rofecoxib from the market. This has been explained by the fact that COX-2 inhibitors don't inhibit platelet thromboxane production but do inhibit endothelial cell prostacyclin production, which constrains platelet activation and counteracts the vasoconstrictive actions of thromboxane $A_2$ generated by platelets. Corticosteroids clearly are anti-inflammatory effects but long term corticosteroid administration can have numerous serious side effects which include adrenal atrophy, resulting in an inability to respond normally to various stresses, increased risk of infection, gastrointestinal bleeding, osteoporosis, weight gain, mood changes, fluid retention resulting in elevated blood pressure, hyperglycemia, cataracts and glaucoma, and aseptic bone necrosis. Accordingly, it is recognized that there is a great need to develop new anti-inflammatory therapeutics. New anti-inflammatory therapeutics under consideration or currently being developed include anti-cytokine therapies, protease inhibitors, inhibition of NF-kB, small molecule inhibitors of signal transduction, inhibition of activated complement, and activation of peroxisome proliferator-activator receptors (PPAR)[33].

Unquestionably, NSAID's exert potent anti-inflammatory effects. However, there are paradoxes in attempts to ascribe the underlying mechanism(s) by which NSAID's exert their anti-inflammatory effects. The prevailing dogma has always been that the antiinflammatory effects of NSAID's can be attributed to their ability to inhibit the formation of the various PGs formed by the different PG synthases, i.e. $PGE_2$, $PGD_2$, etc. However, quite amazingly, it has never been shown that any end product PG or combination of end product PGs actually cause true inflammation. Thus, the equivalent of Koch's postulates have never been fulfilled to support that notion that end product PGs are what cause inflammation. In fact, as mentioned previously, numerous studies have described anti-inflammatory effects of $PGE_2$, $PGD_2$, and $PGI_2$[1-28]. Therein lays a real dilemma that requires explanation. A conclusion in a recent 2009 paper by Scher and Pillinger entitled "The Anti-Inflammatory Effects of Prostaglandins" states: "It is increasingly clear that any paradigm identifying PGs as exclusively proinflammatory is both limited and in need of revision"[18].

Another important aspect of the inflammatory process that is well recognized is that leukocytes are recruited into sites of inflammation. While it is well established that activation of these inflammatory cells upregulates the expression of COX-2 resulting in enhanced PG formation, this also is accompanied by the generation of reactive oxygen species (ROS) by these cells via NADPH oxidases, etc. Accordingly, it has been recognized that oxidative stress is also an important component of inflammation but the reverse is also true in that oxidative stress has also been causally linked the development of inflammation[34].

Therefore, two important questions addressed by the present inventors are (a) why are COX inhibitors anti-inflammatory and (b) is there some common link between products of oxidative stress and products of the COX pathways that promote inflammation. As mentioned, it is difficult to causally attribute the production of enzymatically produced various end products of the COX pathways to inflammation because in aggregate these products have been shown to exert anti-inflammatory effects.

However, there are other products of the COX pathways that have been previously ignored by others. Specifically, these are acyclic γ-ketoaldehyde (γ-KA) products that are formed by non-enzymatic rearrangement of $PGH_2$. These were discovered by Dr. Robert Salomon in 1989 and were shown to rapidly adduct to lysine residues on proteins and undergo further reaction to form extensive protein-protein and DNA cross-links[35, 36]. He termed these compounds levuglandins (LG) $E_2$ and $D_2$ owing to their structurally similarity to levulinic acid (See the following scheme).

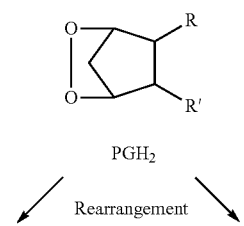

PGH₂

Rearrangement

-continued

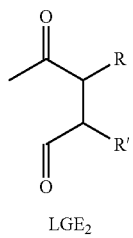
LGE$_2$

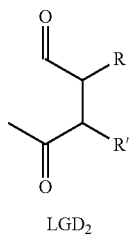
LGD$_2$

In 1990, the present inventors reported the discovery that a series of PGF$_2$-like compounds are formed in abundance in vivo by a non-enzymatic free radical catalyzed mechanism, which we termed F$_2$-isoprostanes (F$_2$-IsoPs)[37]. The present inventors subsequently also showed that LG-like compounds, which were initially termed isolevuglandins and then subsequently isoketals (IsoKs), are also formed in abundance as products of the IsoP pathway by rearrangement of the PGH2-like endoperoxide intermediates in the IsoP pathway[32]. Importantly, instead of just two LGs formed via the COX pathway, there are a total of 64 different γ-KA isomers formed via the IsoP pathway. Herein, these are collectively referred to as COX-derived or IsoP-derived γ-KAs throughout this patent application.

γ-KAs are highly reactive and remarkably injurious molecules. They rapidly (almost instantaneously) adduct specifically to lysine residues on proteins. The chemical pathway involved in this is outlined in the scheme, below.

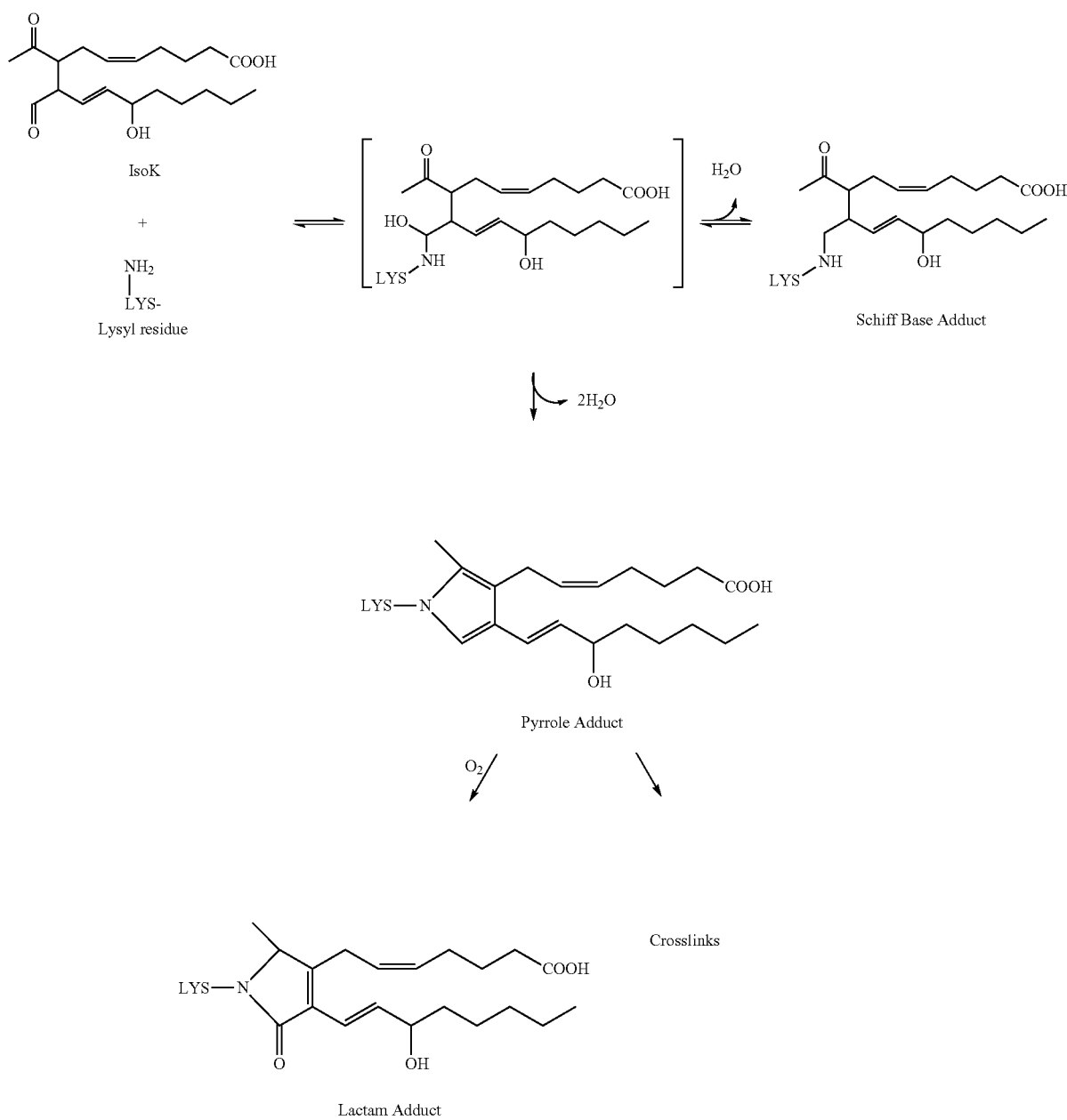

They also adduct to the amine group on phostatidylenthanolamine[38-40]. What is interesting is that these γ-KAs don't simply adduct to lysine residues on proteins, they also exhibit a remarkable proclivity to rapidly induce extensive cross-linking of proteins as shown in FIG. 1 in which a γ-KA was incubated with serum albumin and then analyzed over time by gel electrophoresis.

As seen in FIG. 1, within 10 minutes the appearance of protein dimmers appear followed by the formation of more extensively crosslinked proteins at later time points. The cellular fate of these cross-linked proteins is not well understood. However, the present inventors have shown that (a) they are poorly degraded or not degraded at all by the proteosome, depending on the number of adducts that are present on the protein, and that (b) they also can inhibit the ability of the proteosome to degrade normal protein substrates[41]. In this regard, it has been shown that proteosome inhibition up-regulates inflammatory gene transcription induced by an atypical pathway of NF-κB activation[42]. Therefore, given the potential injurious nature of γ-KA-crosslinked proteins, the present inventors are the first to show that these γ-KAs promote an inflammatory response.

Although many potential mechanisms may underlie how these γ-KAs might be pro-inflammatory, the present inventors have explored one potential novel mechanism which is that these γ-KA adducted self-proteins and cross-linked self-proteins may induce an immune response. Without being bound by theory or mechanism, we discovered that that γ-KA adducted proteins and crosslinked proteins could break immune tolerance and elicit an autoantibody response to normally non-immunogenic self-antigens. If γ-KA adducted proteins are immunogenic this would fuel an immune response to these adducted proteins, which could be highly inflammatory.

Figure 2:
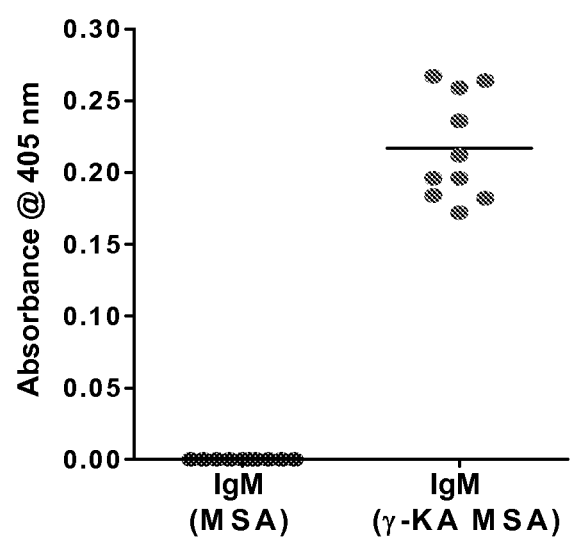
FIG. 2 is a graph that shows antibody binding to γ-KA.

This is demonstrated by the following example, where the present inventors pre-bled and then injected normal and γ-KA adducted mouse serum albumin (MSA) without adjuvant into 25 mice (35 μg/mouse) every 2-3 weeks for several months. Our hypothesis was that mice would not make antibodies to non-adducted MSA but would make antibodies to γ-KA adducted MSA. ELISA was then used to detect different classes of serum antibodies to non-adducted and γ-KA adducted MSA. What was of considerable interest was the discovery that nearly all of the mice prior to injection of γ-KA adducted MSA had circulating serum IgM (but not IgA, IgG, or IgE) antibodies that bound to γ-KA adducted MSA, but not MSA (FIG. 2), indicating the mice naturally produced IgM antibodies to γ-KA adducted MSA.

This is consistent with observations by others that natural IgM antibodies against lipid oxidation-specific epitopes have been described which are thought to play an important protective role by preventing inflammatory reactions induced by the oxidatively modified lipids that they recognize ([43,44]). The present inventors also found that mice immunized with γ-KA adducted MSA produced IgG antibodies to γ-KA adducted MSA and several of these same mice also produced IgG antibodies that bound to non-adducted MSA, while mice immunized with non-adducted MSA did not produce these antibodies.

Figures 3, 4:
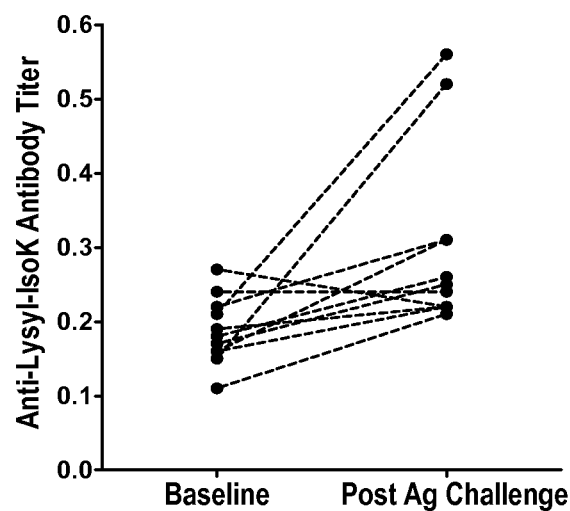
FIG. 3 is a graph that shows antibody titer.
FIG. 4 is a graph that shows antibody titer.

The present inventors have previously shown that levels of γ-KA protein adducts increase in the lung, predominantly in bronchoepitheleal cells, after antigen challenge in sensitized mice[45]. Whether humans have circulating antibodies to γ-KA adducted proteins and whether serum antibody titers increase in an acute setting of oxidative stress and inflammation, which would be associated with enhanced formation of γ-KA adducted proteins was then explored. To answer this question patients with allergic asthma, a disease associated with both enhanced inflammation and oxidative stress were antigen challenged, and assayed bronchoalveolar lavage fluid for antibodies to non-adducted albumin and γ-KA adducted albumin at baseline and 24 hrs after antigen challenge. The present inventors have previously shown in sensitized mice that there is a significant increase in γ-KA protein adducts in the lung after antigen challenge[45]. IgE antibodies to non-adducted albumin were not detected. Notably, however, measurable IgE serum antibody titers against γ-KA adducted albumin were present in all patients at baseline and in all patients but one, IgE (but not IgA, IgG of IgM) antibody titers to γ-KA adducted albumin increased after antigen challenge (FIG. 3).

It is well established that consumption of alcohol in excess causes an oxidative injury to the liver[46]. Moreover, lipid peroxidation epitopes contribute to immune reactions in alcoholic liver disease[47]. Therefore, we also sought to determine if hospitalized patients with alcoholic liver disease had higher serum titers of antibodies against γ-KA lysyl adducts compared to non-alcoholic patients. As shown in (FIG. 4) this was indeed the case. It is of interest and should be pointed out that even the non-alcoholic patients had measurable anti-γ-KA lysyl adduct antibodies, albeit at much lower titers.

The mouse study results show that the present inventors confirmed that adduction γ-KAs to a self-antigen (e.g. albumin) is capable of breaking tolerance to self-antigens and the results of the human study in patients with asthma show that γ-KAs are also involved in the human immune response. Thus, the present inventors suggest that the formation of γ-KAs by COX enzymes and/or the IsoP pathway can adduct to self-antigens and trigger a pathological inflammatory autoimmune response in humans, which should be prevented or diminished by treatment with γ-KA scavengers.

Accordingly, one embodiment of the present invention is preventing such an inflammatory autoimmune response by treatment with γ-KA scavengers, and preferably with the γ-KA scavengers of the present invention.

Another embodiment of the present invention is the identification of compounds that scavenge these γ-KAs, formed via either the IsoP or COX pathways, thereby preventing them from adducting to lysine residues on proteins and other amines i.e aminophospholipids.

One embodiment of the present invention is a method of treating and/or preventing inflammation damage that comprises administering an effective IsoK/NeuroK adduct formation suppressing amount of a phenolic amine compound and/or a salicylamine compound or analog thereof.

Another embodiment of the present invention is a method of preventing or retarding the progression of oxidative stress associated with inflammation comprising administering an effective oxidative stress preventing or decreasing amount of a phenolic amine compound and/or a salicylamine compound or analog thereof.

Another embodiment of the present invention is a method of treating and/or preventing hypertension that comprises administering an effective IsoK/NeuroK adduct formation suppressing amount of a phenolic amine compound and/or a salicylamine compound or analog thereof.

Another embodiment of the present invention is a method of treating and/or preventing psorisis that comprises administering an effective IsoK/NeuroK adduct formation suppressing amount of a phenolic amine compound and/or a salicylamine compound or analog thereof.

Another embodiment of the present invention is a method for the manufacture of a medicament for treating at least one of inflammation, psoriasis, and/or hypertension, comprising combining a compound disclosed herein with a pharmaceutically acceptable carrier.

Another embodiment of the present invention is the use of a compound disclosed herein for treating at least one of inflammation, psoriasis, and/or hypertension.

Examples of compounds of the present invention include, but are not limited to, compounds selected from the formula or analogs thereof, and pharmaceutical salts thereof, and their use as anti-inflammation agents:

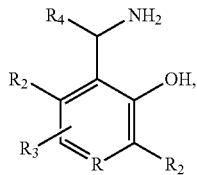

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; or analogs thereof.

Examples of compounds of the present invention include, but are not limited to, compounds selected from the formula or analogs thereof, and pharmaceutical salts thereof, and their use as anti-hypertension agents:

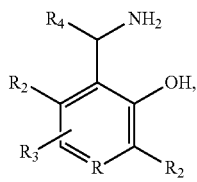

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; or analogs thereof.

Examples of compounds of the present invention include, but are not limited to, compounds selected from the formula or analogs thereof, and pharmaceutical salts thereof, and their use as anti-psoriasis agents:

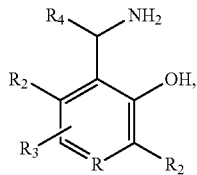

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; or analogs thereof.

DETAILED DESCRIPTION OF THE PRESENT INVENTION

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As can be seen herein, there is overlap in the definition of treating and preventing.

As used herein, the term "diagnosed" means having been subjected to a physical examination by a person of skill, for example, a physician, and found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. For example, a subject can be identified as having a need for treatment of a disorder (e.g., a disorder related to inflammation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "scavenger" or "scavenging" refers to a chemical substance that can be administered in order to remove or inactivate impurities or unwanted reaction products. For example, the isoketals irreversibly adduct specifically to lysine residues on proteins. The isoketal scavengers of the present invention react with isoketals before they adduct to the lysine residues. Accordingly, the compounds of the present invention "scavenge" isoketals, thereby preventing them from adducting to proteins.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "hydroxyl" as used herein is represented by a formula —OH.

The term "nitro" as used herein is represented by a formula —$NO_2$.

The term "pharmaceutically acceptable" describes a material that is not biologically or otherwise undesirable, i.e., without causing an unacceptable level of undesirable biological effects or interacting in a deleterious manner.

As stated above, one embodiment of the present invention is a method of treating, preventing, or ameliorating an inflammatory autoimmune response by treatment with γ-KA scavengers, and preferably with the γ-KA scavengers of the present invention.

Embodiments of the present invention include compounds of the following formula, and their use as anti-inflammation agents:

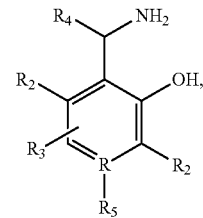

wherein:
R is N or C;
$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

and stereoisomers and analogs thereof.

Other embodiments of the present invention, include compounds of the following formula, and their use as anti-hypertension agents:

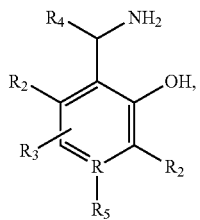

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof.

Other embodiments of the present invention include compounds of the following formula, and their use as anti-psoriasis agents:

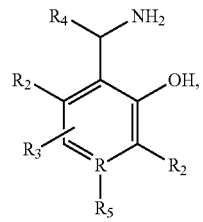

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof.

In other embodiments of the present invention, examples of compounds of the present invention include, but are not limited to, compounds selected from the following formula or analogs thereof, and pharmaceutical salts thereof, and their use as agents described herein:

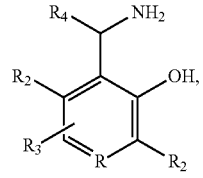

wherein:

R is N or C;

$R_2$ is independently H, substituted or unsubstituted alkyl;

$R_3$ is H, halogen, alkoxy, hydroxyl, nitro;

$R_4$ is H, substituted or unsubstituted alkyl, carboxyl; and stereoisomers and analogs thereof.

In another embodiment of the present invention is a compound selected from the above formula or analogs thereof, and pharmaceutical salts thereof, and their use as anti-inflammation agents, provided that $R_2$ is not —$CH_2$—OH when R is N, $R_4$ is H, and $R_2$ is $CH_3$.

The compounds or analogs may chosen from:

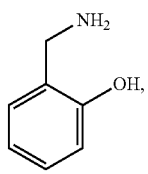

or an analog thereof.

The compounds or analogs may also be chosen from:

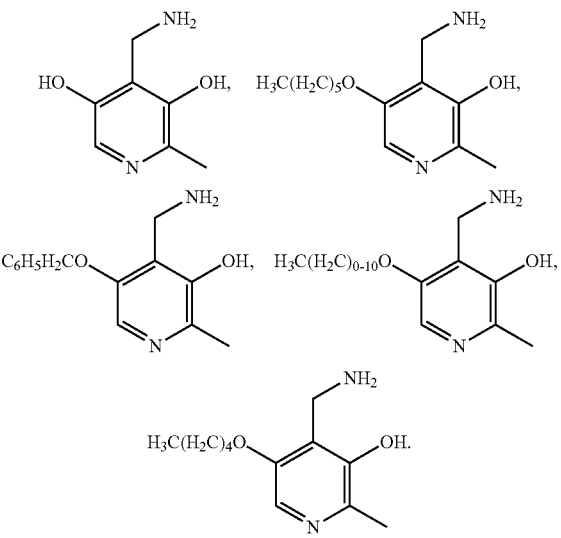

or an analog thereof.

The compounds or analogs may also be chosen from:

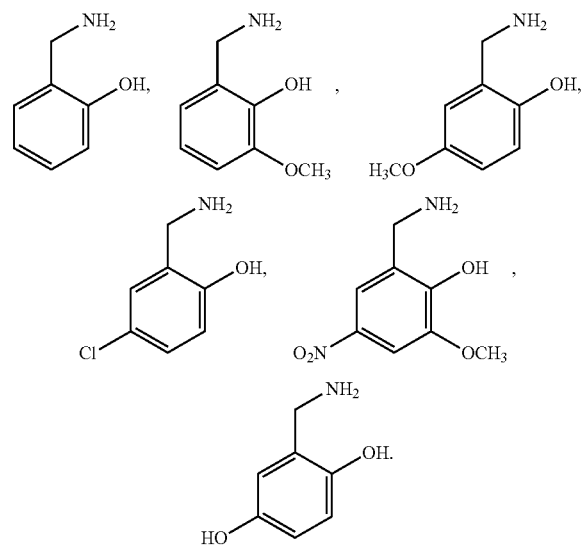

or an analog thereof.

The compounds may also be chosen from:

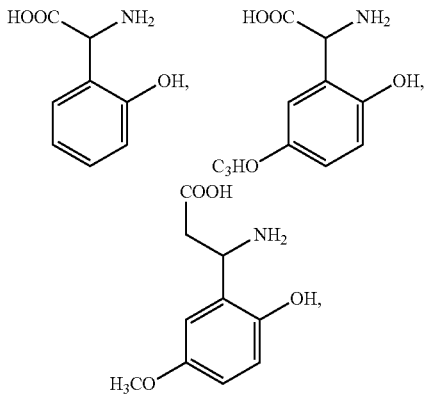

or an analog thereof.

The compounds may also be chosen from

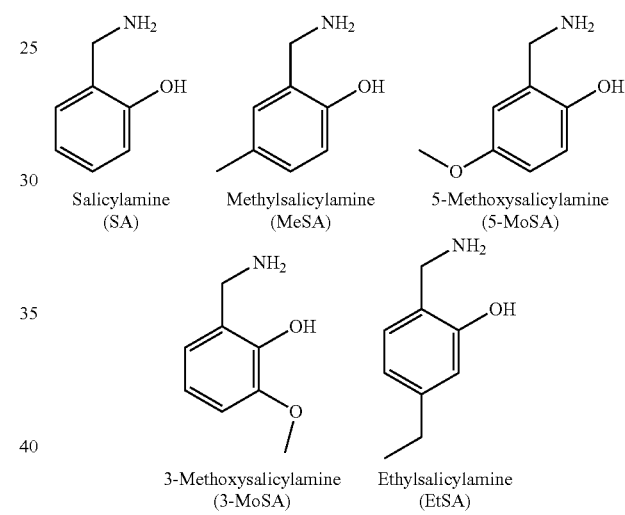

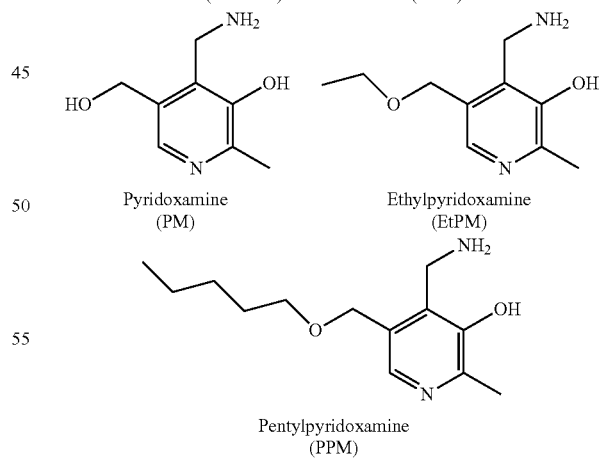

or an analog thereof.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The compounds of the present invention can be administered as the sole active pharmaceutical agent, or can be used in combination with one or more other agents useful for treating or preventing various complications, such as, for example, inflammation and other inflammation-related diseases. When administered as a combination, the therapeutic agents can be formulated as separate compositions that are given at the same time or different times, or the therapeutic agents can be given as a single composition.

As indicated herein, the compounds of the present invention may be made up in a solid form (including granules, powders or suppositories) or in a liquid form (e.g., solutions, suspensions, or emulsions). They may be applied in a variety of solutions and may be subjected to conventional pharmaceutical operations such as sterilization and/or may contain conventional adjuvants, such as preservatives, stabilizers, wetting agents, emulsifiers, buffers etc.

Thus, for administration, the compounds of the present invention are ordinarily combined with one or more adjuvants appropriate for the indicated route of administration. For example, they may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In therapeutic applications, the compounds of the present invention may be administered to a mammalian patient in an amount sufficient to reduce or inhibit the desired indication. Amounts effective for this use depend on factors including, but not limited to, the route of administration, the stage and severity of the indication, the general state of health of the mammal, and the judgment of the prescribing physician. The compounds of the present invention are safe and effective over a wide dosage range. However, it will be understood that the amounts of pyridoxamine actually administered will be determined by a physician, in the light of the above relevant circumstances.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., J. Pharmaceutical Science, 66: 1-19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Another aspect of the present invention is the treatment of inflammatory diseases such as Crohn's disease, inflammatory bowel disease, and ulcerative colitis, asthma, graft versus host disease, chronic obstructive pulmonary disease; autoimmune diseases such as Graves' disease, rheumatoid arthritis, systemic lupus erythematosis, psoriasis.

Another aspect is the use of compounds of the present invention as a substitute for NSAID treatment. Accordingly, aspects of the present invention include methods of treating conditions such as, for example, Rheumatoid arthritis, osteoarthritis, inflammatory arthropathies (e.g. ankylosing spondylitis, psoriatic arthritis, Reiter's syndrome), acute gout, dysmenorrhoea (menstrual pain), metastatic bone pain, headache and migraine, postoperative pain, mild-to-moderate pain due to inflammation and tissue injury, pyrexia (fever), ileus, and renal colic.

In this regard, the compound may be used in place of NSAIDs for (a) treating or reducing inflammation; (b) treating a gastrointestinal disorder; (c) facilitating wound healing; (d) treating or reversing gastrointestinal, renal and/or respiratory toxicity; (e) treating an inflammatory disease; and (f) treating an ophthalmic disorder in a patient in need thereof.

The gastrointestinal disorder may be an inflammatory bowel disease, Crohn's disease, gastritis, irritable bowel syndrome, constipation, ulcerative colitis, a peptic ulcer, a stress ulcer, a bleeding ulcer, gastric hyperacidity, dyspepsia, gastroparesis, Zollinger-Ellison syndrome, gastroesophageal reflux disease, a bacterial infection, short-bowel (anastomosis) syndrome, or a hypersecretory state associated with systemic mastocytosis or basophilic leukemia and hyperhistaminemia. The wound may be an ulcer.

In other embodiments, the inflammatory disease may be a cardiovascular disorder, reperfusion injury to an ischemic organ, angiogenisis, arthritis, asthma, bronchitis, premature labor, tendinitis, bursitis, an autoimmune disease, an immunological disorder, a skin-related condition, neoplasia, an inflammatory process in a disease, pulmonary inflammation, a central nervous system disorder, allergic rhinitis, respiratory distress syndrome, endotoxin shock syndrome, a microbial infection, a bacterial-induced inflammation, a viral induced inflammation, a urinary disorder, a urological disorder, endothelial dysfunction, organ deterioration, tissue deterioration, a sexual dysfunction or activation, adhesion and infiltration of neutrophils at the site of inflammation.

While one embodiment of the present invention includes the use of pyridoxamine, a member of the vitamin B6 family[48], a possible draw back with this embodiment exists in that pyridoxamine is highly polar, given that γ-KAs formed via the IsoP pathway are initially formed in the lipid bilayer.

Other embodiments of the present invention include the use of analogs of pyridoxamine that are less polar but retain the critical molecular structure of this molecule responsible for intercepting γ-KAs[49]. One example is 2-hydroxy-benzylamine (salicylamine, SA) which is 980 times more reactive than lysine with γ-KAs. Importantly, the present inventors have shown that these γ-KA scavengers do not inhibit COX enzymes[49].

After the present inventors' discovery of the IsoP pathway of non-enzymatic free radical catalyzed formation of PG-like compounds, including intermediate $PGH_2$-like endoperoxides, they undertook to explore whether levuglandin-like γ-KAs were also formed via this pathway and showed that indeed they are[32]. These compounds were synthesized and it was observed how potentially injurious these compounds could be. This led the present inventors to consider that inhibition of the formation of these compounds by inhibition of the COX enzymes with NSAID's seemed to be a very plausible hypothesis to explain why NSAID's exerted antiinflammatory effects. This was even more attractive in that reactive oxygen species, etc. are generated in settings of inflammation which cause lipid peroxidation resulting in the formation of endoperoxide $PGH_2$-like intermediates in the IsoP pathway that can also undergo rearrangement to form γ-KAs, which have been termed isolevuglandins or isoketals.

This hypothesis started to become more attractive and more plausible after we developed the highly effective compounds in the present invention that are capable of intercepting these γ-KAs from adducting to proteins and aminophospholipids.

Figure 5:
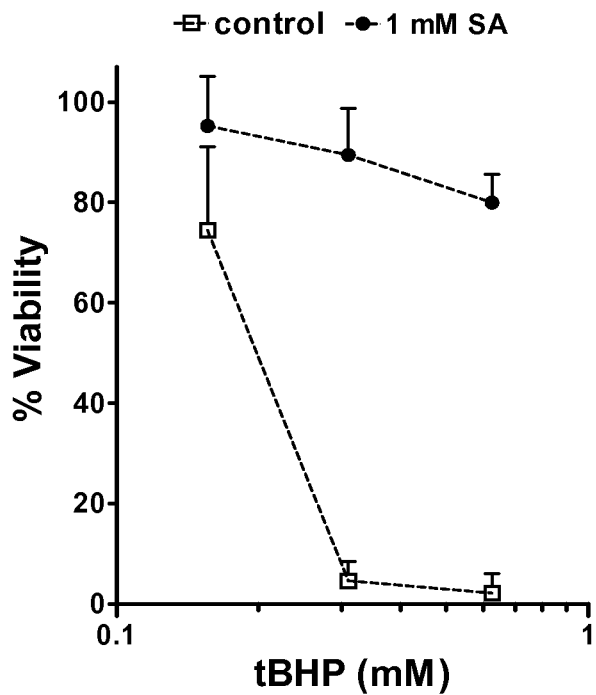
FIG. 5 is a graph that shows cell death after treatment with salicylamine.

One example is shown in FIG. 5, where cells are exposed to a lethal concentration of the oxidant t-butylhydroperoxide. Cells that were treated with salicylamine were almost completely protected against cell death. This strongly suggests that these γ-KAs are a major effecter of oxidative damage, which is also an important component of inflammation. Accordingly, we suspected that the γ-KAs generated by the COX pathways would likely be very pro-inflammatory, which might explain the underlying mechanism by which NSAID's exert some their anti-inflammatory effects.

The present inventors have shown that levels of γ-KA adducts are increased in disease affected areas of whole brain tissue from patients with Alzheimer's disease. Also, using the single chain antibody they were able to show that this increase levels in these brains was primarily localized to neurons, which suggested strongly that these adducts likely may be affecting neuronal function and survival. The present inventors accessed the ability of the γ-KA scavenger salicylamine to prevent the development of cognitive abnormalities in an animal model of human Alzheimer's disease, hAPO4 mice. Treatment of these animals with salicylamine almost completely prevented the development cognitive deficits in these mice.

Since it is very common for elderly patients who are admitted to the hospital with a condition associated with an oxidative and inflammatory insult that should be very treatable, such as pneumonia, often deteriorate into multi-organ failure and die. So we tested the hypothesis that elderly humans may have an impaired capacity to constrain and oxidative insult compared to young individuals. The present inventors have utilized an ischemia/reperfusion insult to the arm in humans to explore this hypothesis and found that indeed older adult humans have a markedly impaired ability to constrain this oxidative insult. This suggests that supplementation of these elderly patients with antioxidants or implementation other approaches to enhance resistance to an oxidative stress may improve outcomes from insults such as pneumonia, etc.

EXAMPLES

In addition to examples shown above, the following examples demonstrate certain embodiments of the present invention. All examples are to be construed as being exemplary of certain aspects of the present invention and are not to be construed as being limiting thereof.

Example 1

As indicated above, one embodiment of the present invention is the use of salicylamine to treat inflammation. To demonstrate this example, a salicyamine compound of the present invention was used to inhibit carrageenin-induced paw edema. The carrageenin-induced paw edema rat model has been probably the most utilized animal model to screen for potency of NSAIDs and other antiinflammatory compounds to inhibit inflammation for decades. For example, see *Proc Soc Exp Biol Med* 111:544 in 1962 by Winter C A et. al., entitled: "Carrageenin-induced edema of the hind paw of the rat as an assay for antiinflammatory drugs". Importantly, it has been shown that this model is one of the most robust predictors of clinical potency of NSAIDs[54].

Figure 6:
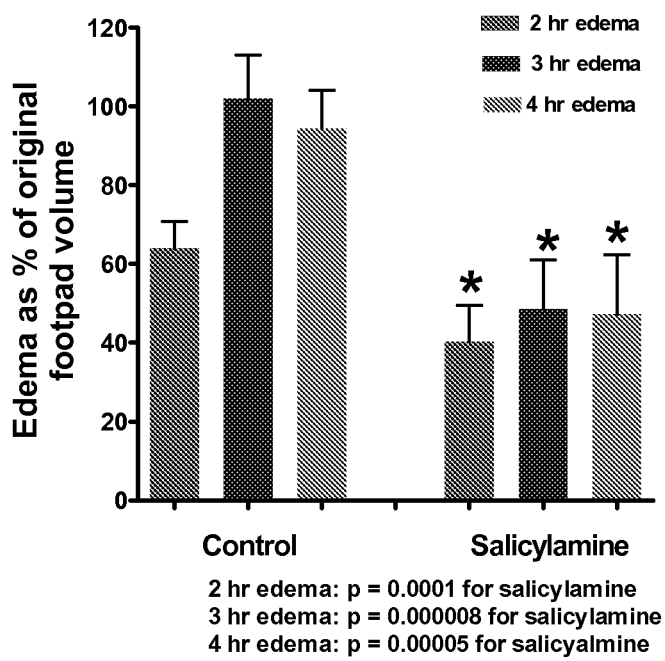
FIGS. 6 and 7 are graphs that show edema calculation.

Our initial experiments tested the ability of a single dose of salicylamine (200 mg/kg), administered intraperitoneally, to reduce paw edema at various time points. Carrageenan (100 μl of a 1% solution in saline) was injected into the hind right footpad. Footpad volume was measured in a water displacement plethysmometer before injection of carrageenin and at 2 hr, 3 hr, and 4 hr post-carrageenin. Edema was calculated as footpad volume change (ml) as a percentage of original paw volume for each individual animal. The results obtained are shown in FIG. 6.

Notably, there was a marked inhibition of carrageenin-induced paw edema by the γ-KA scavenger salicylamine at all time points, which extended out to 4 hrs after the injection of carrageenin. We have defined the pharmacokinetics of salicylamine and found that the half life ($t_{1/2}$) in plasma is quite short ~60 mins) (manuscript in press). Although plasma concentrations of salicylamine are lower than tissue concentrations, it is still notable that after a single intraperitoneal injection of salicylamine that the decrease in paw edema was sustained and persisted out to at least 4 hrs after injection of carrageenin.

Example 2

Figure 7:
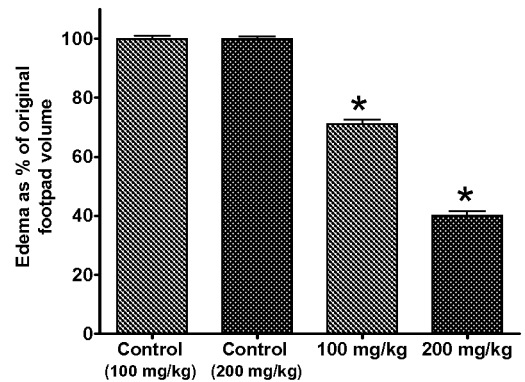

The efficacy an analog of salicylamine, 5-methyl-salicylamine, to inhibit carrageenin-induced paw edema was accessed at 3 hrs after injection of carrageenin at two doses, 200 and 100 mg/kg ip (FIG. 7).

Notably, the effect of 5-methyl-salicylamine to reduce paw edema was dose-dependent with mean reduction in edema of 29% at the dose of 100 mg/kg and 60% at the dose of 200 mg/kg.

Figure 8:
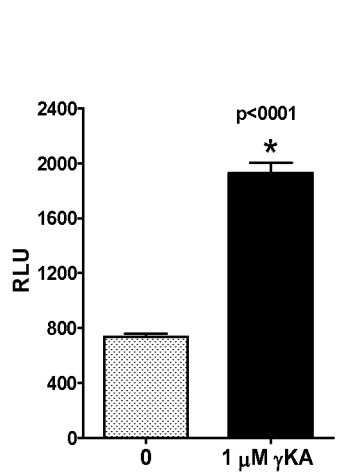
FIG. 8 is a graph that shows induction of NF-κB.

The effect of γ-KAs and salicylamine on induction of NF-κB was explored using a novel luciferase reporter assay to quantitatively monitor the induction of expression of NF-κB both in vitro in cells and in vivo[55; 56]. NF-κB is required for maximal induction of many cytokines which are thought to be important in the generation of the acute inflammatory responses[57]. Accordingly, the downstream effects of an agent that suppresses the induction of NF-κB would be a reduction in the level of inflammation. The first question we asked was does exposure of cells to γ-KAs induce the expression of NF-κB using the luciferase reporter assay mentioned above. In this experiment NF-κB reporter macrophages were incubated with just 1 μMγ-KA for 4 hours and we found that this resulted in an impressive induction of NF-κB (FIG. 8). The abbreviation RLU in this figure stands for Relative Light Units that were measured by luciferase assay.

Example 3

Figure 9:
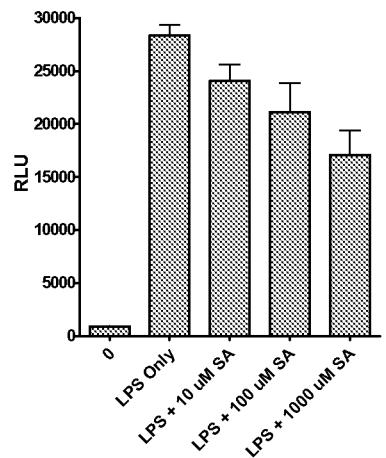
FIG. 9 is graph that shows stepwise reduction of NF-κB.

Another embodiment of the present invention is treatment with varying concentrations of salicylamine (SA) would suppress lipopolysaccharide (LPS) induced expression of NF-κB in NF-κB reporter macrophages. As shown in (FIG. 9), there was a concentration dependent stepwise reduction in the expression of NF-κB, which was highly significant (p<0001).

An in vivo experiment was performed to explore whether treatment with salicylamine would down regulate the activity of NF-kB in animals injected with LPS. The animals we used were mice with a luciferase NF-kB reporter gene developed by Dr. Timothy Blackwell mentioned previously. LPS was injected into mice and salicylamine was injected intraperitoneally at 1 hr, 3 hrs, and 5 hrs after the LPS injection. Lung NF-kB luciferase assay and neutrophil cell counts in lung bronchoalveolar lavage fluid (BAL) were then determined 8 hrs after the LPS injection. There was a reduction in both (a) activity of NF-kB (FIG. 10) (b) and neutrophil cell counts (FIG. 11), both of which are indicative of a pronounced anti-inflammatory effect of salicylamine treatment in these animals.

Example 4

It is important to emphasize that the use of salicylamine is one example of the present invention. Other embodiments include compounds that intercept γ-KA scavengers on various biological processes, their analogs and salt forms thereof. Different non-limiting examples of compounds of the present invention are listed below, which intercept γ-KAs with varying degrees of hydrophilicity. Additionally, to solubilize the more hydrophobic compounds, they have been converted them to an acetate salt. These react with γ-KAs in vitro at a rate more than 2 orders of magnitude greater than the potency of the reaction of γ-KAs with the ε-amine of lysine[49]. None of the compound listed below, including salicylamine, inhibit cyclooxygenase enzymes[49]. Included are analogs, salts, and pharmaceutical compositions comprising compounds that intercept γ-KA scavengers on various biological processes.

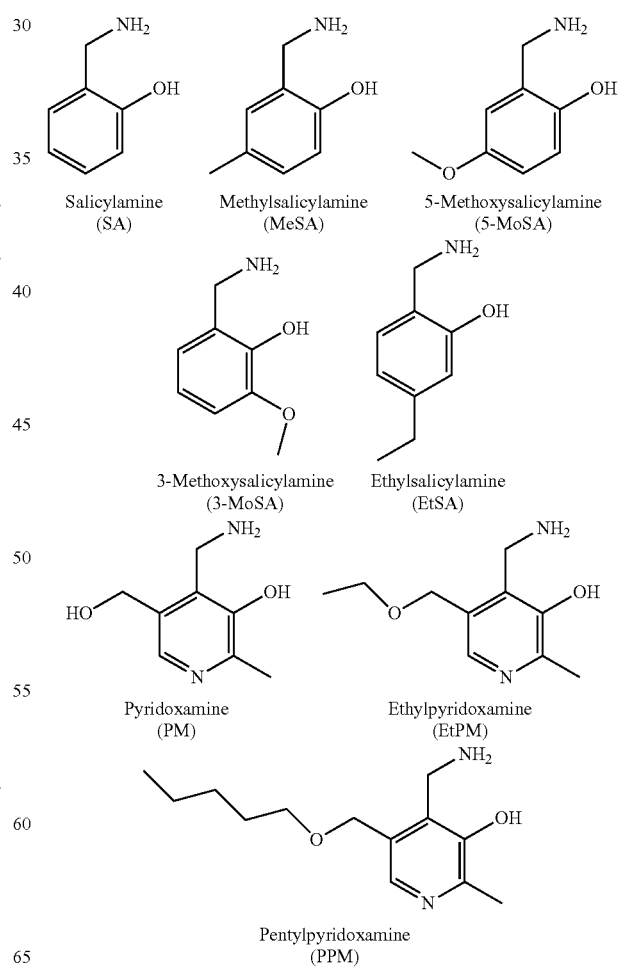

Example 5

This example shows the effect of compounds of the present invention on hypertension. In this example, mice were made hypertensive by an infusion of angiotensin II. As a control, some mice received an infusion of the diluent for angiotensin II (sham). Other mice were treated with salicylamine (SA) or its vehicle. See FIG. 12. In this example, salicylamine was administered in the drinking water at a concentration of 1 gram per liter.

In summary, embodiments of the present invention include compounds that intercept γ-KAs formed via the COX and isoprostane pathways of lipid oxidation, thereby preventing their adduction to proteins and aminophospholipids exert robust antiinflammatory effects. The inventors have shown that the inhibition of the γ-KAs formed from rearrangement of $PGH_2$, rather than PGs formed by PG synthases, explains the preponderance of the antiinflammatory properties of NSAID's. Notably also is that it is well recognized that inflammation is an important component of free radical induced oxidative damage. Accordingly, γ-KAs are also generated as a product of the isoprostane pathway of free radical catalyzed lipid peroxidation. Without being bound by theory or mechanism, the present inventors have discovered that antiinflammatory properties of γ-KA scavengers, which scavenge γ-KAs formed via both the COX and isoprostane pathways, are efficacious than inhibiting only the formation of γ-KAs formed via the COX pathways with NSAIDs.

LITERATURE CITED

1. Ajuebor, M. N., Singh, A., and Wallace, J. L. (2000). Cyclooxygenase-2-derived prostaglandin D(2) is an early anti-inflammatory signal in experimental colitis. Am J Physiol Gastrointest Liver Physiol 279, G238-244.
2. Bonazzi, A., Bolla, M., Buccellati, C., Hernandez, A., Zarini, S., Vigano, T., Fumagalli, F., Viappiani, S., Ravasi, S., Zannini, P., et al. (2000). Effect of endogenous and exogenous prostaglandin E(2) on interleukin-1 beta-induced cyclooxygenase-2 expression in human airway smooth-muscle cells. Am J Respir Crit. Care Med 162, 2272-2277.
3. Caggiano, A. O., and Kraig, R. P. (1999). Prostaglandin E receptor subtypes in cultured rat microglia and their role in reducing lipopolysaccharide-induced interleukin-1 beta production. J Neurochem 72, 565-575.
4. Gilroy, D. W., Colville-Nash, P. R., Willis, D., Chivers, J., Paul-Clark, M. J., and Willoughby, D. A. (1999). Inducible cyclooxygenase may have anti-inflammatory properties. Nat Med 5, 698-701.
5. Giri, S., Rattan, R., Singh, A. K., and Singh, I. (2004). The 15-deoxy-delta12,14-prostaglandin J2 inhibits the inflammatory response in primary rat astrocytes via down-regulating multiple steps in phosphatidylinositol 3-kinase-Akt-NF-kappaB-p300 pathway independent of peroxisome proliferator-activated receptor gamma. J Immunol 173, 5196-5208.
6. Hashimoto, K., Ethridge, R. T., Saito, H., Rajaraman, S., and Evers, B. M. (2003). The PPARgamma ligand, 15d-PGJ2, attenuates the severity of cerulein-induced acute pancreatitis. Pancreas 27, 58-66.
7. Haworth, O., and Buckley, C. D. (2007). Resolving the problem of persistence in the switch from acute to chronic inflammation. Proc Natl Acad Sci USA 104, 20647-20648.
8. Hilliard, M., Frohnert, C., Spillner, C., Marcone, S., Nath, A., Lampe, T., Fitzgerald, D. J., and Kehlenbach, R. H. The anti-inflammatory prostaglandin 15-deoxy-delta(12, 14)—PGJ2 inhibits CRM1-dependent nuclear protein export. J Biol Chem 285, 22202-22210.
9. Ianaro, A., Ialenti, A., Maffia, P., Di Meglio, P., Di Rosa, M., and Santoro, M. G. (2003). Anti-inflammatory activity of 15-deoxy-delta12,14-PGJ2 and 2-cyclopenten-1-one: role of the heat shock response. Mol Pharmacol 64, 85-93.
10. Idzko, M., Hammad, H., van Nimwegen, M., Kool, M., Vos, N., Hoogsteden, H. C., and Lambrecht, B. N. (2007). Inhaled iloprost suppresses the cardinal features of asthma via inhibition of airway dendritic cell function. J Clin Invest 117, 464-472.
11. Jiang, G. L., Im, W. B., Donde, Y., and Wheeler, L. A. Comparison of prostaglandin E2 receptor subtype 4 agonist and sulfasalazine in mouse colitis prevention and treatment. J Pharmacol Exp Ther 335, 546-552.
12. Min, S. Y., Kim, W. U., Cho, M. L., Hwang, S. Y., Park, S. H., Cho, C. S., Kim, J. M., and Kim, H. Y. (2002). Prostaglandin E2 suppresses nuclear factor-kappaB mediated interleukin 15 production in rheumatoid synoviocytes. J Rheumatol 29, 1366-1376.
13. Mochizuki, M., Ishii, Y., Itoh, K., Iizuka, T., Morishima, Y., Kimura, T., Kiwamoto, T., Matsuno, Y., Hegab, A. E., Nomura, A., et al. (2005). Role of 15-deoxy delta(12,14) prostaglandin J2 and Nrf2 pathways in protection against acute lung injury. Am J Respir Crit. Care Med 171, 1260-1266.
14. Muller, T., Durk, T., Blumenthal, B., Herouy, Y., Sorichter, S., Grimm, M., Panther, E., Cicko, S., Norgauer, J., and Idzko, M. Iloprost has potent anti-inflammatory properties on human monocyte-derived dendritic cells. Clin Exp Allergy 40, 1214-1221.
15. Park, E. J., Park, S. Y., Joe, E. H., and Jou, I. (2003). 15d-PGJ2 and rosiglitazone suppress Janus kinase-STAT inflammatory signaling through induction of suppressor of cytokine signaling 1 (SOCS1) and SOCS3 in glia. J Biol Chem 278, 14747-14752.
16. Pirianov, G., Waddington, S. N., Lindstrom, T. M., Terzidou, V., Mehmet, H., and Bennett, P. R. (2009). The cyclopentenone 15-deoxy-delta 12,14-prostaglandin J(2) delays lipopolysaccharide-induced preterm delivery and reduces mortality in the newborn mouse. Endocrinology 150, 699-706.
17. Rajakariar, R., Hilliard, M., Lawrence, T., Trivedi, S., Colville-Nash, P., Bellingan, G., Fitzgerald, D., Yagoob, M. M., and Gilroy, D. W. (2007). Hematopoietic prostaglandin D2 synthase controls the onset and resolution of acute inflammation through PGD2 and 15-deoxyDelta12 14 PGJ2. Proc Natl Acad Sci USA 104, 20979-20984.
18. Scher, J. U., and Pillinger, M. H. (2009). The anti-inflammatory effects of prostaglandins. J Investig Med 57, 703-708.
19. Soberman, R. J., and Christmas, P. (2006). Revisiting prostacyclin: new directions in pulmonary fibrosis and inflammation. Am J Physiol Lung Cell Mol Physiol 291, L142-143.
20. Strassheim, D., Riddle, S. R., Burke, D. L., Geraci, M. W., and Stenmark, K. R. (2009). Prostacyclin inhibits IFN-gamma-stimulated cytokine expression by reduced recruitment of CBP/p300 to STAT1 in a SOCS-1-independent manner. J Immunol 183, 6981-6988.
21. Takagi, T., Naito, Y., Ichikawa, H., Tomatsuri, N., Katada, K., Isozaki, Y., Kuroda, M., Kokura, S., Yoshida, N., and Yoshikawa, T. (2004). A PPAR-gamma ligand, 15-deoxy-Delta12,14-prostaglandin J(2), inhibited gastric mucosal injury induced by ischemia-reperfusion in rats. Redox Rep 9, 376-381.
22. Takahashi, Y., Tokuoka, S., Masuda, T., Hirano, Y., Nagao, M., Tanaka, H., Inagaki, N., Narumiya, S., and Nagai, H. (2002). Augmentation of allergic inflammation in prostanoid IP receptor deficient mice. Br J Pharmacol 137, 315-322.
23. Takaishi, O., Arakawa, T., Fujiwara, Y., Fukuda, T., Otani, K., Yamasaki, K., Higuchi, K., and Kuroki, T. (1999). Inhibition by 16,16-dimethyl prostaglandin E2 of tumor necrosis factor-alpha and interleukin-1 beta production and messenger RNA expression in human monocytes stimulated by *Helicobacter pylori*. Dig Dis Sci 44, 2405-2411.
24. Ulivi, V., Cancedda, R., and Cancedda, F. D. (2008). 15-deoxy-delta 12,14-prostaglandin J(2) inhibits the synthesis of the acute phase protein SIP24 in cartilage: Involvement of COX-2 in resolution of inflammation. J Cell Physiol 217, 433-441.
25. Vong, L., Ferraz, J. G., Panaccione, R., Beck, P. L., and Wallace, J. L. A pro-resolution mediator, prostaglandin D(2), is specifically up-regulated in individuals in long-term remission from ulcerative colitis. Proc Natl Acad Sci USA 107, 12023-12027.
26. Vunta, H., Davis, F., Palempalli, U. D., Bhat, D., Arner, R. J., Thompson, J. T., Peterson, D. G., Reddy, C. C., and Prabhu, K. S. (2007). The anti-inflammatory effects of selenium are mediated through 15-deoxy-Delta12,14-prostaglandin J2 in macrophages. J Biol Chem 282, 17964-17973.
27. Zhou, W., Hashimoto, K., Goleniewska, K., O'Neal, J. F., Ji, S., Blackwell, T. S., Fitzgerald, G. A., Egan, K. M., Geraci, M. W., and Peebles, R. S., Jr. (2007). Prostaglandin I2 analogs inhibit proinflammatory cytokine production and T cell stimulatory function of dendritic cells. J Immunol 178, 702-710.
28. Zimmer, M., Lamb, J., Ebert, B. L., Lynch, M., Neil, C., Schmidt, E., Golub, T. R., and Iliopoulos, O. The connectivity map links iron regulatory protein-1-mediated inhibition of hypoxia-inducible factor-2a translation to the anti-inflammatory 15-deoxy-delta12,14-prostaglandin J2. Cancer Res 70, 3071-3079.
29. Flower, R. J., Harvey, E. A., and Kingston, W. P. (1976). Inflammatory effects of prostaglandin D2 in rat and human skin. Br J Pharmacol 56, 229-233.
30. Kingston, W. P., and Greaves, M. W. (1985). Actions of prostaglandin E2 metabolites on skin microcirculation. Agents Actions 16, 13-14.
31. Salomon, R. G., and Miller, D. B. (1985). Levuglandins: isolation, characterization, and total synthesis of new secoprostanoid products from prostaglandin endoperoxides. Adv Prostaglandin Thromboxane Leukot Res 15, 323-326.
32. Brame, C. J., Salomon, R. G., Morrow, J. D., and Roberts, L. J., 2nd. (1999). Identification of extremely reactive gamma-ketoaldehydes (isolevuglandins) as products of the isoprostane pathway and characterization of their lysyl protein adducts. J Biol Chem 274, 13139-13146.
33. Dinarello, C. A. Anti-inflammatory Agents: Present and Future. Cell 140, 935-950.
34. Gill, R., Tsung, A., and Billiar, T. Linking oxidative stress to inflammation: Toll-like receptors. Free Radic Biol Med 48, 1121-1132.
35. Iyer, R. S., Ghosh, S., and Salomon, R. G. (1989). Levuglandin E2 crosslinks proteins. Prostaglandins 37, 471-480.
36. Murthi, K. K., Friedman, L. R., Oleinick, N. L., and Salomon, R. G. (1993). Formation of DNA-protein crosslinks in mammalian cells by levuglandin E2. Biochemistry 32, 4090-4097.
37. Morrow, J. D., Hill, K. E., Burk, R. F., Nammour, T. M., Badr, K. F., and Roberts, L. J., 2nd. (1990). A series of prostaglandin F2-like compounds are produced in vivo in humans by a non-cyclooxygenase, free radical-catalyzed mechanism. Proc Natl Acad Sci USA 87, 9383-9387.
38. Bernoud-Hubac, N., Fay, L. B., Armarnath, V., Guichardant, M., Bacot, S., Davies, S. S., Roberts, L. J., 2nd, and Lagarde, M. (2004). Covalent binding of isoketals to ethanolamine phospholipids. Free Radic Biol Med 37, 1604-1611.
39. Sullivan, C. B., Matafonova, E., Roberts, L. J., 2nd, Amarnath, V., and Davies, S. S. Isoketals form cytotoxic phosphatidylethanolamine adducts in cells. J Lipid Res 51, 999-1009.
40. Li, W., Laird, J. M., Lu, L., Roychowdhury, S., Nagy, L. E., Zhou, R., Crabb, J. W., and Salomon, R. G. (2009). Isolevuglandins covalently modify phosphatidylethanolamines in vivo: detection and quantitative analysis of hydroxylactam adducts. Free Radic Biol Med 47, 1539-1552.
41. Davies, S. S., Amarnath, V., Montine, K. S., Bernoud-Hubac, N., Boutaud, O., Montine, T. J., and Roberts, L. J., 2nd. (2002). Effects of reactive gamma-ketoaldehydes formed by the isoprostane pathway (isoketals) and cyclooxygenase pathway (levuglandins) on proteasome function. FASEB J 16, 715-717.
42. Cullen, S. J., Ponnappan, S., and Ponnappan, U. Proteasome inhibition up-regulates inflammatory gene transcription induced by an atypical pathway of NF-kappaB activation. Biochem Pharmacol 79, 706-714.
43. Chou, M. Y., Hartvigsen, K., Hansen, L. F., Fogelstrand, L., Shaw, P. X., Boullier, A., Binder, C. J., and Witztum, J. L. (2008). Oxidation-specific epitopes are important targets of innate immunity. J Intern Med 263, 479-488.
44. Binder, C. J. Natural IgM antibodies against oxidation-specific epitopes. J Clin Immunol 30 Suppl 1, S56-60.
45. Talati, M., Meyrick, B., Peebles, R. S., Jr., Davies, S. S., Dworski, R., Mernaugh, R., Mitchell, D., Boothby, M., Roberts, L. J., 2nd, and Sheller, J. R. (2006). Oxidant stress modulates murine allergic airway responses. Free Radic Biol Med 40, 1210-1219.
46. Kang, Y. J., and Zhou, Z. (2005). Zinc prevention and treatment of alcoholic liver disease. Mol Aspects Med 26, 391-404.
47. Mottaran, E., Stewart, S. F., Rolla, R., Vay, D., Cipriani, V., Moretti, M., Vidali, M., Sartori, M., Rigamonti, C., Day, C. P., et al. (2002). Lipid peroxidation contributes to immune reactions associated with alcoholic liver disease. Free Radic Biol Med 32, 38-45.
48. Amarnath, V., Amarnath, K., Davies, S., and Roberts, L. J., 2nd. (2004). Pyridoxamine: an extremely potent scavenger of 1,4-dicarbonyls. Chem Res Toxicol 17, 410-415.
49. Zagol-Ikapitte, I., Amarnath, V., Bala, M., Roberts, L. J., 2nd, Oates, J. A., and Boutaud, O. Characterization of scavengers of gamma-ketoaldehydes that do not inhibit prostaglandin biosynthesis. Chem Res Toxicol 23, 240-250.
50. Nahrendorf, M., Pittet, M. J., and Swirski, F. K. Monocytes: protagonists of infarct inflammation and repair after myocardial infarction. Circulation 121, 2437-2445.

51. Agostinho, P., Cunha, R. A., and Oliveira, C. Neuroinflammation, oxidative stress and the pathogenesis of Alzheimer's disease. Curr Pharm Des 16, 2766-2778.
52. Moore, K. P., Holt, S. G., Patel, R. P., Svistunenko, D. A., Zackert, W., Goodier, D., Reeder, B. J., Clozel, M., Anand, R., Cooper, C. E., et al. (1998). A causative role for redox cycling of myoglobin and its inhibition by alkalinization in the pathogenesis and treatment of rhabdomyolysis-induced renal failure. J Biol Chem 273, 31731-31737.
53. Holt, S., Reeder, B., Wilson, M., Harvey, S., Morrow, J. D., Roberts, L. J., 2nd, and Moore, K. (1999). Increased lipid peroxidation in patients with rhabdomyolysis. Lancet 353, 1241.
54. Mukherjee, A., Hale, V. G., Borga, O., and Stein, R. (1996). Predictability of the clinical potency of NSAIDs from the preclinical pharmacodynamics in rats. Inflamm Res 45, 531-540.
55. Stathopoulos, G. T., Sherrill, T. P., Han, W., Sadikot, R. T., Polosukhin, V. V., Fingleton, B., Yull, F. E., and Blackwell, T. S. (2008). Use of bioluminescent imaging to investigate the role of nuclear factor-kappaBeta in experimental non-small cell lung cancer metastasis. Clin Exp Metastasis 25, 43-51.
56. Sadikot, R. T., and Blackwell, T. S. (2008). Bioluminescence: imaging modality for in vitro and in vivo gene expression. Methods Mol Biol 477, 383-394.
57. Wong, E. T., and Tergaonkar, V. (2009). Roles of NF-kappaB in health and disease: mechanisms and therapeutic potential. Clin Sci (Lond) 116, 451-465.
58. Davies, S. S., Amarnath, V., Brame, C. J., Boutaud, O., and Roberts, L. J., 2nd. (2007). Measurement of chronic oxidative and inflammatory stress by quantification of isoketal/levuglandin gamma-ketoaldehyde protein adducts using liquid chromatography tandem mass spectrometry. Nat Protoc 2, 2079-2091.
59. Kasuga, K., Yang, R., Porter, T. F., Agrawal, N., Petasis, N. A., Irimia, D., Toner, M., and Serhan, C. N. (2008). Rapid appearance of resolvin precursors in inflammatory exudates: novel mechanisms in resolution. J Immunol 181, 8677-8687.

The invention thus being described, it would be obvious that the same can be varied in many ways. Such variations that would be obvious to one of ordinary skill in the art is to be considered as being bard of this disclosure.

Unless otherwise indicated, all numbers expressing quantities of ingredients, properties such as reaction conditions, and so forth used in the Specification are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:
1. A method of treating or ameliorating an isoprostane induced inflammatory autoimmune response, comprising administering a gamma-ketoaldehyde scavenging effective amount to a patient in need thereof a compound of the following formula:

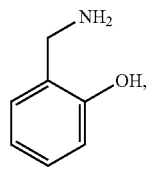

and stereoisomers and pharmaceutically acceptable salts thereof,
wherein the inflammatory autoimmune response includes at least one of hypertension, psoriasis, or edema.

2. A method of treating hypertension, comprising administering to a patient in need thereof an effective amount of a compound of the following formula:

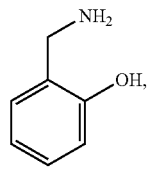

and stereoisomers and pharmaceutically acceptable salts thereof.

3. A method of treating hypertension, comprising co-administering to a patient in need thereof a gamma-ketoaldehyde scavenging effective amount of a compound of the following formula:

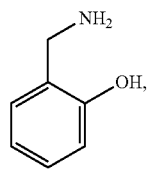

and stereoisomers and pharmaceutically acceptable salts thereof, with an additional pharmaceutical agent known for at least one of treating inflammation, treating an isoprostane-induced autoimmune response, and reducing hypertension.

4. The method of claim 1, wherein the co-administration is separate compositions given at the same time or at different times.

5. A method of treating psoriasis, comprising administering to a patient in need thereof an effective amount of a compound of the following formula:

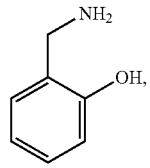

and stereoisomers and pharmaceutically acceptable salts thereof.

* * * * *